United States Patent
Lowe et al.

(10) Patent No.: US 10,751,320 B2
(45) Date of Patent: Aug. 25, 2020

(54) THERAPEUTIC AGENTS CONTAINING CANNABIS FLAVONOID DERIVATIVES FOR THE PREVENTION AND TREATMENT OF NEURODEGENERATIVE DISORDERS

(71) Applicants: FLAVOCURE BIOTECH, LLC, Columbia, MD (US); Henry I C Lowe, Kingston (JM); Ngeh J. Toyang, Columbia, MD (US)

(72) Inventors: Henry I C Lowe, Kingston (JM); Ngeh J. Toyang, Columbia, MD (US)

( * ) Notice: Subject to any disclaimer, the term of this patent is extended or adjusted under 35 U.S.C. 154(b) by 0 days.

(21) Appl. No.: 15/742,294

(22) PCT Filed: Jul. 8, 2016

(86) PCT No.: PCT/US2016/041507
§ 371 (c)(1),
(2) Date: Jan. 5, 2018

(87) PCT Pub. No.: WO2017/027136
PCT Pub. Date: Feb. 16, 2017

(65) Prior Publication Data
US 2019/0083452 A1    Mar. 21, 2019

Related U.S. Application Data

(60) Provisional application No. 62/190,011, filed on Jul. 8, 2015.

(51) Int. Cl.
*A61K 31/352* (2006.01)
*A61K 47/10* (2017.01)
(Continued)

(52) U.S. Cl.
CPC ............ *A61K 31/352* (2013.01); *A61K 47/10* (2013.01); *A61K 47/26* (2013.01); *A61K 47/32* (2013.01);
(Continued)

(58) Field of Classification Search
CPC .................................................. A61K 31/352
See application file for complete search history.

(56) References Cited

U.S. PATENT DOCUMENTS

| 7,025,992 B2 | 4/2006 | Whittle |
| 7,083,814 B2 | 8/2006 | Ilic |
| 9,044,390 B1 * | 6/2015 | Speier .................... A61K 36/00 |

FOREIGN PATENT DOCUMENTS

WO    WO/2002/064109    8/2002

OTHER PUBLICATIONS

Turner, C. E., Elsohly, M. A., & Boeren, E. G, "Constituents of Cannabis Sativa L. XVII., A review of the natural constituents", Journal of Natural Products, 43(2), 169-234 (1980).
(Continued)

*Primary Examiner* — San Ming R Hui
(74) *Attorney, Agent, or Firm* — Royal W. Craig; Gordon Feinblatt LLC

(57) ABSTRACT

The present invention provides a cannabis-based flavonoid pharmaceutical composition including any one or more selected from the group of Apigenin, Cannflavin A, Cannflavin B, Cannflavin C, Chrysoeriol, Cosmosiin, Flavocannabiside, Kaempferol, Luteolin, Myricetin, Orientin, Isoorientin (Homoorientin), Quercetin, (+)-Taxifolin, Vitexin, and Isovitexin, or their synthases, for the prevention and treatment of certain diseases of the CNS system and related disorders.

5 Claims, 4 Drawing Sheets

(51) Int. Cl.
  A61K 47/26    (2006.01)
  A61K 47/32    (2006.01)
  A61P 25/28    (2006.01)
  A61P 25/08    (2006.01)
  A61P 25/16    (2006.01)

(52) U.S. Cl.
  CPC ............... A61P 25/08 (2018.01); A61P 25/16 (2018.01); A61P 25/28 (2018.01)

(56) References Cited

OTHER PUBLICATIONS

Sauer, M. A., Rifka, S. M., Hawks, R. L., Cutler, G. B., & Loriaux, D. L., "Journal of Pharmacology and Experimental Therapeutics", 224(2), 404-407 (1983).

Offord, E. A., Macé, K., Avanti, O., & Pfeifer, A. M, "Mechanisms Involved in the Chemoprotective Effects of Rosemary Extract Studied in Human Liver and Bronchial Cells", Cancer Letters, 114(1), 275-281, (1997).

McPartland, J. M., & Pruitt, P. L. "Side effects of pharmaceuticals not elicited by comparable herbal medicines: thr case of tetrahydrocannabinol and marijuana". Alternative Therapies in Health & Medicine 5(4):57-62, (1999).

Gomez-Nicola D, Perry VH, Analysis of microglial proliferation in Alzheimer's disease, Methods Mol. Biol., 2016;1303:185-93, 2013.

Olmos-Alonso, A., Schetters, S. T., Sri, S., Askew, K., Mancuso, R., Vargas-Caballero, M., . . . & Gomez-Nicola, D. Pharmacological targeting of CSF1R inhibits microglial proliferation and prevents the progression of Alzheimer's-like pathology. Brain, awv379, (2016).

Bruijn, L. I., Miller, T. M. & Cleveland, D. W. Unraveling the mechanisms involved in motor neuron degeneration in ALS. Annual review of neuroscience, 27, 723-749, (2004).

Martínez-Muriana, A., Mancuso, R., Francos-Quijorna, I., Olmos-Alonso, A., Osta, R., Perry, V. H., . . . & López-Vales, R., CSF1R blockade slows the progression of amyotrophic lateral sclerosis by reducing microgliosis and invasion of macrophages into peripheral nerves. Scientific reports, 6, (2016).

Ueda, S., Yamashita, H., Hikiami, R., Sawamoto, N., Yoshida, K., & Takahashi, R. A novel A792D mutation in the CSF1R gene causes hereditary diffuse leukoencephalopathy with axonal spheroids characterized by slow progression. eNeurologicalSci, 1(1), 7-9, (2015).

Rademakers, R., Baker, M., Nicholson, A. M., Rutherford, N. J., Finch, N., Soto-Ortolaza, A., . . . & Adamson, J. Mutations in the colony stimulating factor 1 receptor (CSF1R) gene cause hereditary diffuse leukoencephalopathy with spheroids. Nature genetics, 44(2), 200-205, (2012).

Axelsson R, Roytta M, Sourander P, Akesson HO, Andersen O. Hereditary diffuse leucoencephalopathy with spheroids. Acta Psychiatr Scand Suppl. 314:1-65. [PubMed: 6595937] (1984).

Perez DI, Gil C., Martinez A. Protein kinases CK1 and CK2 as new targets for neurodegenerative diseases, Med Res Rev, 31, 924-54, (2011).

Rebholz, H., Nishi, A., Liebscher, S., Nairn, A. C., Flajolet, M., & Greengard, P. CK2 negatively regulates Gas signaling. Proceedings of the National Academy of Sciences, 106(33), 14096-14101 (2009).

Gerfen, C. R. D1 dopamine receptor supersensitivity in the dopamine-depleted striatum animal model of Parkinson's disease. The Neuroscientist, 9(6), 455-462, (2003).

Chen, X., Wales, P., Quinti, L., Zuo, F., Moniot, S., Herisson, F., . . . & Maxwell, M. M. The sirtuin-2 inhibitor AK7 is neuroprotective in models of Parkinson's disease but not amyotrophic lateral sclerosis and cerebral ischemia. PloS one, 10(1), e0116919, (2015).

Di Fruscia, P., Zacharioudakis, E., Liu, C., Moniot, S., Laohasinnarong, S., Khongkow, M., . . . & Jung, M. The Discovery of a Highly Selective 5, 6, 7, 8-Tetrahydrobenzo [4, 5] thieno [2, 3-d] pyrimidin-4 (3H)-one SIRT2 Inhibitor that is Neuroprotective in an in vitro Parkinson's Disease Model. ChemMedChem, 10(1), 69-82, (2015).

* cited by examiner

Table 2.

| | Results of the inhibition of kinases by cannabis flavonoids and their analogs | | | | | | | | | |
|---|---|---|---|---|---|---|---|---|---|---|
| | Compound Kd/ IC$_{50}$ (nM) | | | | | | | | | |
| Kinase | FBL-03A | FBL-03B | FBL-03C | FBL-03D | FBL-03E | FBL-03F | FBL-03G | FBL-03H | FBL-GS70 | FBL-GS71 |
| CK2α1 | 740 | 768 | 58 | - | >100 | >100 | >100 | >100 | 65.2 | 319 |
| CK2α2 | 350 | 477 | 19 | - | >100 | >100 | >100 | >100 | 4.06 | 137 |
| DYRK1/ DYRK1A | - | - | 36 | >10 | >100 | >100 | >100 | >100 | 82.6 | 40 |
| DYRK1B | - | - | 22.6 | - | >100 | >100 | >100 | >100 | 42.1 | 60 |
| FMS | >10 | 199 | 4 | >10 | >100 | >100 | >100 | >100 | 24 | 16.4 |
| PIM-1 | - | - | 78 | >100 | >100 | >100 | >100 | >100 | 229 | 219 |
| PIM-2 | - | - | - | - | >100 | >100 | >100 | >100 | | |
| PIM-3 | - | 173 | 35 | - | >10 | >10 | >100 | >100 | 11.7 | 34 |

Table 3. Results of the inhibition of SIRTs by cannabis flavonoids and their analogs

| | Compound IC$_{50}$ (μM) | | | | | | |
|---|---|---|---|---|---|---|---|
| Sirtuins | FBL-03A | FBL-03B | FBL-03C | FBL-03D | FBL-03E | FBL-03F | Suramin |
| SIRT1 | 19.01 | 27.44 | 39.45 | - | >100 | >100 | 0.961 |
| SIRT2 | 2.57 | 10.78 | 14.01 | 2.38 | >10 | >10 | 11.65 |
| SIRT3 | - | - | - | - | >50 | >50 | |
| SIRT5 | 122.7 | 104.4 | 132.1 | - | >50 | >50 | 43.65 |

FIG. 3

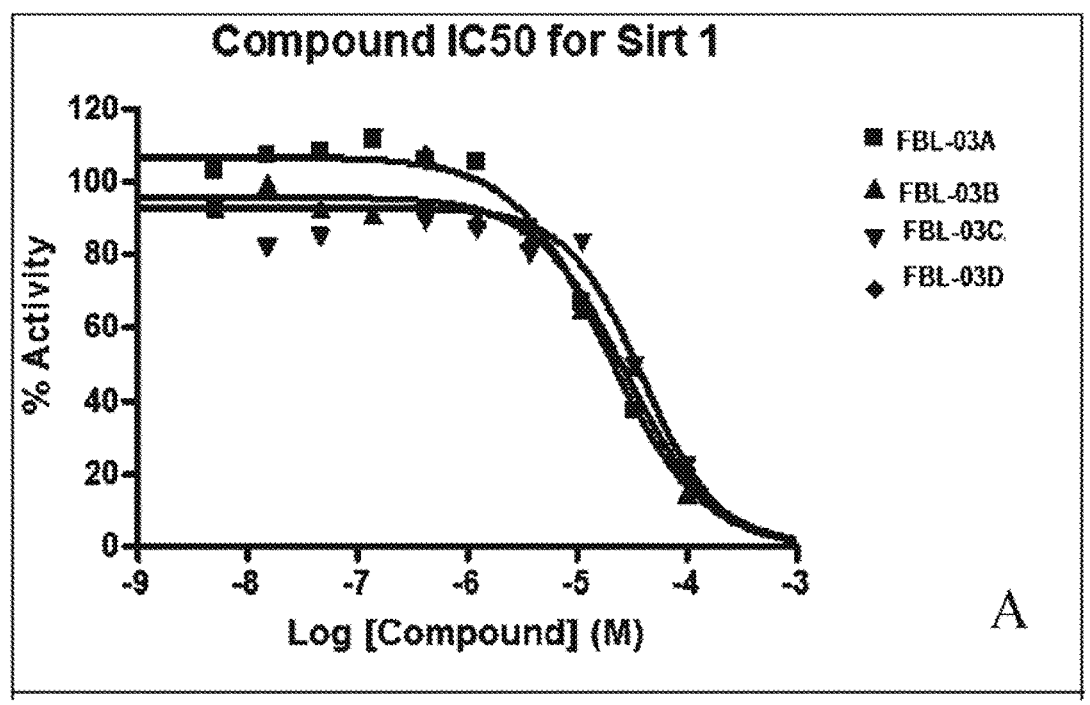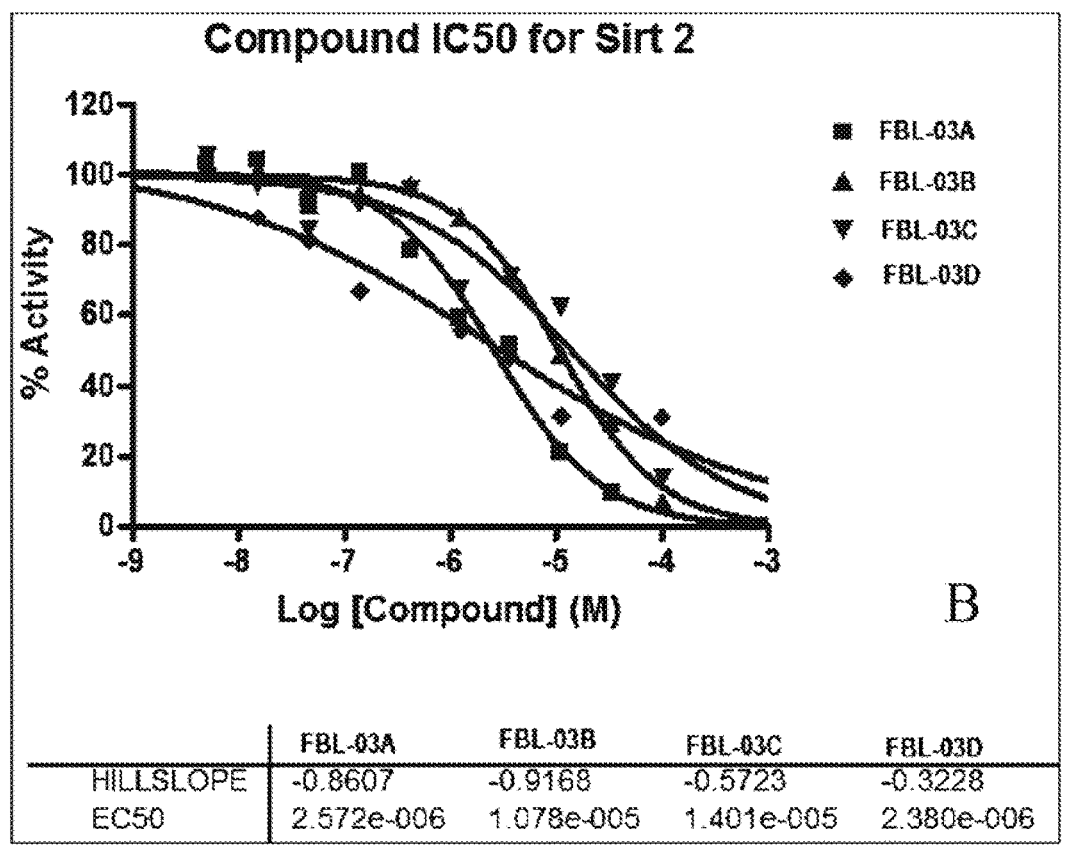
FIG. 4

THERAPEUTIC AGENTS CONTAINING CANNABIS FLAVONOID DERIVATIVES FOR THE PREVENTION AND TREATMENT OF NEURODEGENERATIVE DISORDERS

CROSS-REFERENCE TO RELATED APPLICATIONS

The present application derives priority from U.S. Provisional Patent Application 62/190,011 filed 8 Jul. 2015.

BACKGROUND OF THE INVENTION

1. Field of the Invention

The present invention relates to flavonoid derivatives and, more particularly, to cannabis flavonoid derivatives or the pharmaceutically acceptable salt thereof that may be used in a pharmaceutical composition for preventing and creating CNS related disease particularly Parkinson's, Alzheimer, Huntington's disease, Multiple sclerosis, Amyotrophic lateral sclerosis (ALS), Hereditary diffuse leukoencephalopathy with spheroids (HDLS) and epilepsy.

2. Description of the Background

Flavonoids are common constituents of plants and cover a wide range of functions including acting as yellow pigments in petals and leaves to attract pollinating insects. They might also appear as bluish pigments (anthocyanins) to receive certain wavelengths of light, which permits the plant to be aware of the photoperiod. Many of these flavonoids also protect the plants by being involved in the filtering of harmful ultraviolet light. Some flavonoids play crucial roles in establishing symbiotic fungi, while at the same time they fight infections caused by pathogenic fungi.

Flavonoids have relevant pharmacological activities such as; antioxidant, antidiabetic, anti-inflammatory, antiallergic, antibiotic, antidiarrheal, CNS and against cancer.

Cannabis is credited to have several beneficial pharmacological properties. Unfortunately much attention on Cannabis is focused on its recreational use as a psychoactive drug. Studies have identified over twenty flavonoids in the Cannabis plant, such as; cannflavin A, cannflavin B, cannflavin C, chrysoeril, cosmosiin, flavocannabiside, vitexin, isovitexin, apigenin, kaempferol, myricetin, quercetin, luteolin, homoorientin and orientin (Turner, C. E., Elsohly, M. A., & Boeren, E. G., "Constituents of Cannabis Saliva L. XVII., A review of the natural constituents", *Journal of Natural Products*, 43(2), 169-234 (1980). The distribution of these flavonoids in the plant varies depending on the type of flavonoid. The total content of flavonoids in the Cannabis' leaves and flowers can reach 1-2.5% of its dry weight depending on environment factors and the variety of the plant.

Cannabis flavonoids have been shown to have several pharmacological properties. Apart from the specific pharmacologic properties identified, cannabis flavonoids are thought to play synergistic roles with other metabolites in the plant. For example, some flavonoids are volatile, lipophilic, permeate membranes, and seem to retain pharmacological properties in cannabis smoke (Sauer, M. A., Rifka, S. M., Hawks, R. L., Cutler, G. B., & Loriaux, D. L. "*Journal of Pharmacology and Experimental Therapeutics*", 224(2), 404-407 (1983). Flavonoids may modulate the pharmacokinetics of THC, via a mechanism shared by CBD, the inhibition of P450 3A11 and P450 3A4 enzymes. These two related enzymes metabolize environmental toxins from procarcinogens to their activated forms. P450-suppressing compounds as such serve as chemoprotective agents, shielding healthy cells from the activation of benzo[α]pyrene and aflatoxin B1 (Offord, E. A., Macé, K., Avanti, O., & Pfeifer, A. M., "Mechanisms Involved In The Chemoprotective Effects Of Rosemary Extract Studied In Human Liver And Bronchial Cells"; *Cancer Letters*, 114(1), 275-281, (1997), which are two procarcinogenic agents found in cannabis smoke (McPartland, J. M., & Pruitt, P. L., "*Alternative Therapies In Health And Medicine*", 5(4), 57 (1999). Cannabis flavonoids thus may be modulating the therapeutic effects of THC and CBDs by either synergistically enhancing desired pharmacologic effects or reducing detrimental effects.

Research indicates that the colony stimulating factor 1 receptor (CSF1R) kinase play important roles in microglial activation and proliferation in the brain (Gomez-Nicola et al., 2013). Inhibition of CSF1R provide beneficial effects on the progression of chronic neurodegeneration, highlighting the detrimental contribution of microglial proliferation (Gomez-Nicola D, Perry V H, Analysis of microglial proliferation in Alzheimer's disease, Methods Mol. Biol 2016; 1303; 185-93 2013). Prolonged inhibition of CSF1R in APP/PS1 mice by an orally available tyrosine kinase inhibitor (GW2580) was shown to result in the blockade of microglial proliferation and shifting of the microglial inflammatory profile to an anti-inflammatory phenotype (Olmos-Alonso, A., Schetters, S. T., Sri, S., Askew, K., Mancuso, R., Vargas-Caballero, M., Gomez-Nicola, D., Pharmacological Targeting of CSF1R Inhibits Microglial Proliferation And Prevents The Progression Of Alzheimer's-Like Pathology. *Brain*, awv379, 2016). Targeting of CSF1R in APP/PS1 mice resulted in an improved performance in memory and behavioral tasks and a prevention of synaptic degeneration (Olmos-Alonso et al, supra, 2016). Amyotrophic lateral sclerosis (ALS) is one of the indications that CSF1R has been implicated in its onset and progression. ALS is a fetal neurodegenerative disease caused by the loss of motoneurons in the motor cortex, brainstem and spinal cord. It manifests with skeletal muscle weakness, spasticity and eventual paralysis, leading to the death of patients by respiratory failure 3 to 5 years after diagnosis (Bruijn, L. I., Miller, T. M. & Cleveland, D. W., Unraveling The Mechanisms Involved In Motor Neuron Degeneration In ALS. *Annual review of neuroscience* 2004, 27, 723-749, 2004).

Inflammation is a common neuropathological feature in several neurological disorders, including ALS and the contribution of CSF1R signalling to inflammation in ALS, as a pathway has been reported to control the expansion and activation of microglial cells (Martínez-Muriana, A., Mancuso, R., Francos-Quijorna, I., Olmos-Alonso, A., Osta, R., Perry, V. H., . . . & López-Vales, R., CSF1R Blockade Slows The Progression Of Amyotrophic Lateral Sclerosis By Reducing Microgliosis And Invasion Of Macrophages Into Peripheral Nerves, *Scientific reports*, 6, 2016). New data as such suggest, that CSF1R signalling could be a novel therapeutic target in ALS (Martínez-Muriana et al, supra, 2016).

Hereditary diffuse leukoencephalopathy with spheroids (HDLS) is another indication that CSF1R plays a role it is onset and progression (Ueda, S., Yamashita, H., Hikiami, R., Sawamoto, N., Yoshida, K., & Takahashi, R., A Novel A792D Mutation in the CSF1R Gene Causes Hereditary Diffuse Leukoencephalopathy With Axonal Spheroids Characterized By Slow Progression. *eNeurologicalSci*, 1(1), 7-9, 2015; Rademakers, R., Baker, M., Nicholson, A. M., Rutherford, N. J., Finch, N., Soto-Ortolaza, A. & Adamson, J., Mutations In The Colony Stimulating Factor 1 Receptor (CSF1R) Gene Cause Hereditary Diffuse Leukoencephalopathy With Spheroids, *Nature genetics,* 44(2), 200-205, 2012). HDLS is an autosomal dominantly inherited central nervous system white matter disease with variable clinical presentations including personality and behavioral changes, dementia, depression, parkinsonism, seizures, and others (Axelsson R, Roytta M, Sourander P, Akesson H O, Andersen O. Hereditary Diffuse Leucoencephalopathy With Spheroids, Acta Psychiatr Scand Suppl. 1984; 314:1-65. [PubMed: 6595937, 2009). Given the role of CSF1R in microgial proliferation and differentiation in the brain and the role that microglial plays in HDLS pathogenesis, inhibition of CSF1R is a potential therapeutic target for HDLS and related neurodegenerative diseases. The casein kinase is another important group of kinases implicated in the pathogenesis of neurodegenerative disorders including especially Parkinson's Disease and Alzheimer's (Perez D I, Gil C., Martinez A., Protein Kinases CK1 and CK2 As New Targets For Neurodegenerative Diseases, Med Res Rev, 31, 924-54, 2011). It has been shown that and imbalance in dopamine 1 and 5 receptors mediates Parkinson's Disease and the receptors are negatively regulated by the overexpression of casein kinase 2 (Rebholz, H., Nishi, A., Liebscher, S., Nairn, A. C., Flajolet, M., & Greengard, P., CK2 Negatively Regulates Gas Signaling, *Proceedings of the National Academy of Sciences,* 106(33), 14096-14101, 2009; Gerfen, C. R., D1 Dopamine Receptor Supersensitivity In The Dopamine-Depleted Striatum Animal Model Of Parkinson's Disease, *The Neuroscientist,* 9(6), 455-462, 2003). Casein kinase inhibitors as such hold, promise as potential therapeutic agents against neurodegenerative diseases.

The sirtuins represents another class of proteins that act like double edge swords and in some cases negatively contribute to the pathogenesis of some neurodegenerative disorders. Sirtuins are a class of enzymes believed to play a significant role in diseases of aging, including type 2 diabetes and obesity. SIRT 2 is one of the seven human sirtuin enzymes. Compounds that block the activity of this enzyme could have clinical utility to treat a range of neurodegenerative such as Parkinson's Disease and Huntington's Disease. Using SIR2 inhibitors various researchers have been able to demonstrate that the inhibitors have a neuroprotective effect in models of Parkinson'S Disease (Chen, X., Wales, P., Quinti, L., Zuo, F., Moniot, S., Herisson, F., & Maxwell, M. M., The Sirtuin-2 Inhibitor AK7 Is Neuroprotective In Models Of Parkinson's Disease But Not Amyotrophic Lateral Sclerosis And Cerebral Ischemia, *PloS one,* 10(1), e0116919, 2015; Di Fruscia, P., Zacharioudakis, E., Liu, C., Moniot, S., Laohasinnarong, S., Khongkow, M., & Jung, M., The Discovery of a Highly Selective 5,6,7,8-Tetrahydrobenzo[4,5]thieno[2,3-d]pyrimidin-4 (3H)-one SIRT2 Inhibitor that is Neuroprotective in an in vitro Parkinson's Disease Model, *ChemMedChem,* 10(1), 69-82, 2015).

Given the plethora of evidence supporting the health benefits of cannabis flavonoids, the present inventors have successfully synthesized rare cannabis flavonoids including cannflavin A, cannflavin B and cannflavin C, isocannflavin B and their analogs and have proven CNS efficacy by various pharmacologic assays including activity against key kinases and proteins required for the onset and progression of various CNS related conditions including Parkinson's, Alzheimer, Huntington's disease, Multiple sclerosis, Amyotrophic lateral sclerosis (ALS), Hereditary diffuse leukoencephalopathy with spheroids (HDLS) and epilepsy. It is noteworthy to mention that even though cannflavin A has been isolated from other plant sources, it is only cannabis that has been shown to harbor all three cannflavins. The present invention relates to the use of the newly synthesized flavonoids alone or in combination with other flavonoids or related bioactive compounds particularly the cannabinoids to treat or prevent diseases shown to be inhibited by the use of these flavonoids and the drug combinations.

SUMMARY OF THE INVENTION

It is, therefore, an object of the invention to provide a pharmaceutical composition for the prevention and treatment of, CNS related disease, and other diseases with specific cannabis-based flavonoid compounds.

It is still another object to provide a method for synthesizing said specific cannabis-based flavonoid pharmaceutical compositions.

In accordance with the foregoing objects, the present invention provides a flavonoid-based pharmaceutical composition for the prevention and treatment of CNS disorders having the structure of the general formula of FIG. 1 or a pharmaceutically acceptable salt thereof.

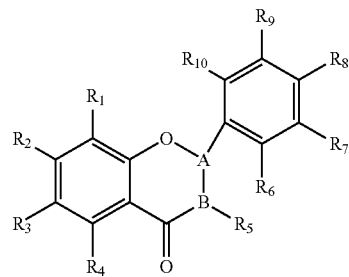

FIG. 1

Wherein,

R1-R10 may be none or any one or more substituents selected from the group consisting of a hydrogen molecule (H), a hydroxide molecule (OH), a methyl group comprising one carbon atom bonded to three hydrogen atoms (CH3), an alkoxy group (O—CH3), a carboxyl group (COOH), chlorine (Cl), Bromine (Br), Fluorine (F) Glutamic acid (Glu), geranyl chain, prenyl chain and any salts or derivatives of the foregoing, A and B may each be either a single or double bond.

A method for the prevention and treatment of CNS related disease, and other diseases is also disclosed using the specific cannabis-based flavonoid pharmaceutical compositions above is also disclosed, as well as a method for isolating the specific flavonoid-based pharmaceutical compositions from raw plant, material and a method for synthesizing said flavonoid-based pharmaceutical compositions.

The present invention is described in greater detail in the detailed description of the invention, and the appended drawings. Additional features and advantages of the invention will be set forth in the description that follows, will be apparent from the description, or may be learned, by practicing the invention.

BRIEF DESCRIPTION OF THE DRAWINGS

Other objects, features, and advantages of the present invention will become more apparent from the following detailed description of the preferred embodiments and certain modifications thereof when taken together with the accompanying drawings in which:

FIG. 3 illustrates results of the inhibition of kinases by cannabis flavonoids and their analogs (Table 2) and results of the inhibition of SIRTs by cannabis flavonoids and their analogs (Table 3).

FIG. 4 is the dose response curves of compounds against Sirtuins.

DETAILED DESCRIPTION OF THE PREFERRED EMBODIMENTS

Reference will now be made in detail to preferred embodiments of the present invention, examples of which are illustrated in the accompanying drawings. Wherever possible, the same reference numbers will be used throughout the drawings to refer to the same or like parts.

The present invention is a group of cannabis-based flavonoid pharmaceutical compositions selected from among the group of Apigenin, Cannflavin A, Cannflavin B, Cannflavin C, Chrysoeriol, Cosmosiin, Flavocannabiside, Kaempferol, Luteolin, Myricetin, Orientin, Isoorientin (Homoorientin), Quercetin, (+)-Taxifolin, Vitexia, and Isovitexin, useful for the prevention and treatment of certain diseases of the CNS system and related disorders.

Figure 1:
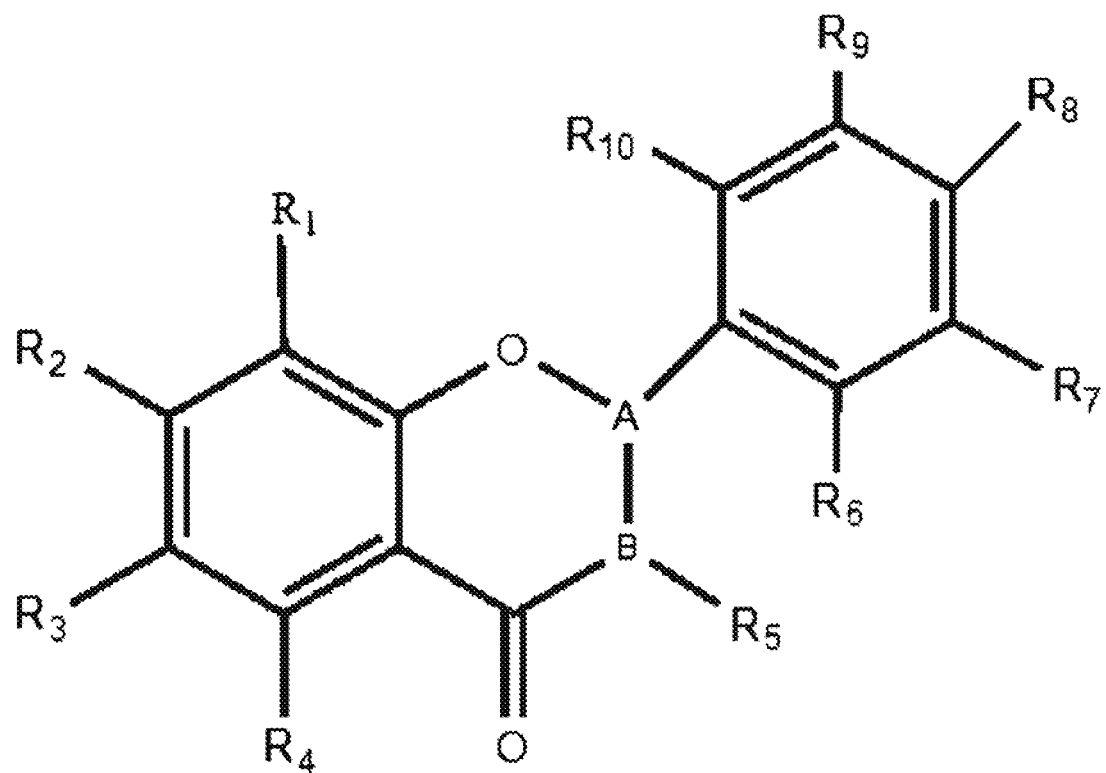
FIG. 1 is an illustration of the general cannabis-based flavonoid pharmaceutical compositions according to the present invention.
Figure 2:
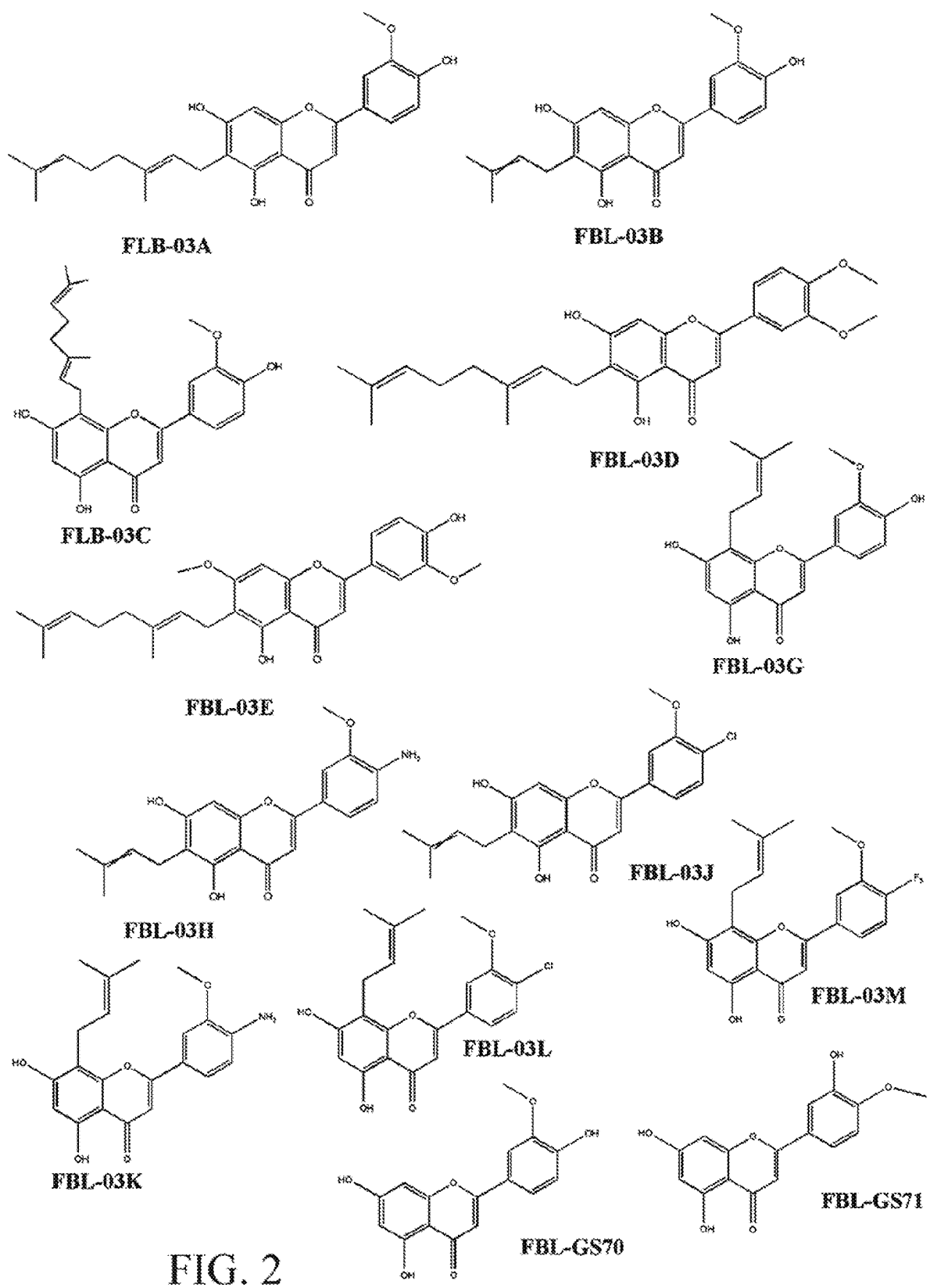
FIG. 2 is the structure of synthesized compounds

The cannabis-based flavonoid pharmaceutical composition for the prevention and treatment of diseases has the structure of the general formula of FIG. 1 or a pharmaceutically acceptable salt thereof.

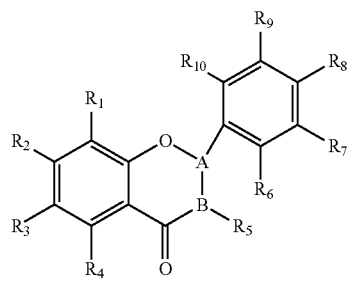

FIG. 1

Wherein,

R1-R10 may be branchless or branch to any one or more substituents selected from the group consisting of a hydrogen molecule (H), a hydroxide molecule (OH), a methyl group comprising one carbon atom bonded to three hydrogen atoms (CH3), an alkoxy group (O—CH3), a carboxyl group (COOH), chlorine (Cl), Bromine (Br), Fluorine (F), Glutamic acid (Glu), and any salts or derivatives of the foregoing. A and B may each be either a single or double bond.

These flavonoids have specifically been shown to inhibit key kinases or proteins involved in the onset and progression of Alzheimer's Disease, Parkinson's Disease, Huntington's Disease, Multiple Sclerosis and epilepsy (as shown below in Table 1).

TABLE 1

Kinase and CNS disease association

| Kinase | CNS disease association |
|---|---|
| CK2α1 | Parkinson's Disease, Alzheimer |
| CK2α2 | Parkinson's Disease, Alzheimer |
| DYRK1/DYRK1A | Alzheimer's |
| DRK1B | CNS |
| FMS (CSF1R) | Parkinson's, Alzheimer, Huntington's disease, Multiple sclerosis, Frontal temporal dementias, traumatic brain iniury, Ischaemic stroke, Amyotrophic lateral sclerosis (ALS), Hereditary diffuse leukoencephalopathy with spheroids (HDLS) and epilepsy. |
| PIM-1 | — |
| PIM-2 | — |
| PIM-3 | — |

The structures of the synthesized flavonoids are presented in FIG. 3 and their related bioactivity is presented in ensuing sections.

In an embodiment, a method for the prevention and treatment of CNS disorders using the specific cannabis-based flavonoid pharmaceutical compositions above is also disclosed. Administration may be by various routes including oral, rectal or intravenous, epidural muscle, subcutaneous, intrauterine, or blood vessels in the brain (intracerebroventricular) injections. The flavonoid derivatives of the general formula (FIG. 1) according to the present invention and a pharmaceutically acceptable salt thereof may be administered in an effective dose, depending on the patient's condition and body weight, extent of disease, drug form, route of administration, and duration, within a range of from 0.1 to 500 mg between 1-6 times a day. Of course, most dosages will be by a carrier. The specific dose level and carrier for patients can be changed according to the patient's weight, age, gender, health status, diet, time of administration, method of administration, rate of excretion, and the severity of disease.

The composition may be formulated for external topical application, oral dosage such as powders, granules, tablets, capsules, suspensions, emulsions, syrups, aerosols, suppositories, or in the form of a sterile injectable solution. Acceptable carriers and excipients may comprise lactose, dextrose, sucrose, sorbitol, mannitol, xylitol, erythritol, maltitol, starches, gum acacia, alginate, gelatin, calcium phosphate, calcium silicate, cellulose, methyl cellulose, microcrystalline cellulose, polyvinylpyrrolidone, water, methyl benzoate, propyl benzoate, talc, magnesium stearate, and mineral oil.

Bioactivity of the above-described compounds has been verified by use of kinase inhibition and histone deacetylaze assays to determine the effect of the cannabis flavonoids in the onset and progression of various CNS related conditions particularly Parkinson's and Alzheimer.

Kinase Inhibition Assay

Cannabis flavonoids and their analogs were subjected to kinase inhibition assay. The compounds were first screened at a single concentration: of 10 μM in the primary assay. Compounds inhibiting at least, 70% of specific kinases were subjected to further screening to determine kd values. To determine the kd values, competition binding assays were established, authenticated and executed as described previously (Fabian et al., 2005, Karaman et al., 2008). For most assays, kinases were fused to T7 phage strains (Fabian et al. 2005) and for the other assays, kinases were produced in HEK-293 cells after which they were tagged with DMA for quantitative PCR detection (data not shown). In general, full-length constructs were used for small, single domain kinases, and catalytic domain constructs for large multi-domain kinases, the binding assays utilized streptavidin-coated magnetic beads treated with biotinylated small molecule ligands for 30 minutes at room temperature which generated affinity resins for the kinase assays. The liganded beads were blocked with excess biotin and washed with blocking buffer (SeaBlock (Pierce), 1% BSA, 0.05% Tween 20, 1 mM DTT) to remove unbound ligand and to reduce non-specific phage binding. Binding reactions were assembled by combining kinases, liganded affinity beads, and test compounds in 1× binding buffer (20% SeaBlock, 0.17×PBS, 0.05% Tween 20, 6 mM DTT), Test compounds were prepared as 40× stocks in 100% DMSO and diluted directly into the assay (Final DMSO concentration=2.5%). All reactions were performed in polypropylene 384-well plates in a final volume of 0.04 ml. The assay plates were incubated at room temperature with shaking for 1 hour and the affinity beads were washed with wash buffer (1×PBS, 0.05% Tween 20). The heads were then re-suspended in elution buffer (1×PBS, 0.05% Tween 20, 0.5 µM non-biotinylated affinity ligand) and incubated at room temperature with shaking for 30 minutes. The kinase concentration in the elunates was measured by quantitative PCR. Kd values were determined using a standard dose response curve using the hill equation. Curves were fitted using a non-linear least square fit with the Levenberg-Marquardt algorithm. FIG. 4 illustrates results of the inhibition of kinases by cannabis flavonoids and their analogs (Table 2).

SIRT Inhibition Assay

SIRT2 displays NAD+-dependent deacetylase activity in an endpoint, trypsin-coupled reaction with a fluorogenic substrate. The deacetylation reaction is performed in 50 mM Tris-HCl, pH 8.0, 137 mM NaCl, 2.7 mM, KCl, 1 mM MgCl2, 1 mg/ml BSA, with Ac-RHK-K(Ac)-AMC and NAD+ as substrates (Km's are ~200 and 500 µM respectively). The reaction is terminated and fluorescence signal (Ex. 360 nm/Em. 460 nm) developed (~30 min.) by addition of an equal volume of 2 mM nicotinamide, 16 mg/mL trypsin in 50 mM. Tris-HCl, pH 8.0, 137 mM NaCl, 2.7 mM KCl, 1 mM MgCl2. FIG. 4 illustrates results of the inhibition of SIRTs by cannabis flavonoids and their analogs (Table 3).

FIG. 5 is the dose response curves of compounds against Sirtuins.

Overcoming the difficulty of delivering therapeutic agents to specific regions of the brain presents a major challenge to treatment of most brain disorders as ~100% of large-molecule neurotherapeutics and more than 98% of all small-molecule drugs fail to cross the BBB (Pardridge 2005). Several flavonoids, due to their low molecular weight and lipophilic properties, are known to cross the BBB and play significant roles in neurotherapeutics (Jäger and Saaby 2011, Faria et al., 2010 and 2014). Preliminary studies using the MPTP induced Parkinson's model, suggested that molecules in this invention likely crossed the BBB and have neuro-protective properties. Following treatment of MPTP Parkinson's induced mice with the compounds, immunohisto-chemistry revealed increase in tyrosine hydroxylase (TH) positive cells in the brain compared to the control confirming the entry and neuroprotective activity of the molecules in the brain (Data not shown).

A method for isolating the specific cannabis-based flavonoid pharmaceutical compositions from raw plant material is also disclosed.

At step 10 an appropriate amount of plant biomass is collected. For present purposes, Cannabis sativa plants were collected by hand. See, Radwan, M. M., ElSohly, M. A., Slade, D., Ahmed, S. A., Wilson, L., El-Alfy, A. T., Khan, I. A., Ross, S. A., 2008a. Non-cannabinoid constituents from a high potency Cannabis sativa variety. Phytochemistry 69, 2627-2633 and Radwan, M. M., Ross, S. A., Slade, D., Ahmed, S. A., Zulfiqar, F., ElSohly, M. A., 2008b. Isolation and characterization of new cannabis constituents from a high potency variety. Planta Med, 74, 267-272. The collected plant material was air dried under shade and pulverized into powder.

At step 20 the powder is subjected to supercritical fluid extraction (SFE) by which carbon dioxide ($CO^2$) is used for separating one component (the extractant) from another (the matrix). The extract is evaporated to dryness resulting in a green residue.

At step 30, for experimental purposes, a bioassay-guided fractionation was employed, using a standard protocol to isolate a pure chemical agent from its natural origin. This entailed a step-by-step separation of extracted components based on differences in their physicochemical properties, and assessing ail their biological activity. The extracted components may, for example, be fractionated by dry column flash chromatography on Si gel using hexane/CH2Cl2/ethyl acetate and mixtures of increasing polarity to yield different fractions. The sample is then degassed by ultra-sonication to yield an insoluble solid, which solid is then filtered. The sample may then be subjected to high performance liquid chromatography (HPLC) using a column Phenomenex Luna™ C18, 5 µm, 2×50 mm; eluent, acetonitrile with 0.05% MeOH to confirm the presence of the various fractions.

At step 40, bioactivity of the extracts were verified in a kinase inhibition assay as described above. This identified the bioactive flavonoids from all the supercritical fluid extracts (SFE). As reported previously, the identified cannabis-based flavonoid extracts showed activity against several kinases implicated in the pathogenesis of CNS disorders.

The next step was to identify the cannabis-based flavonoid constituents responsible for the observed kinase inhibitory activities and to further isolate them.

At step 50 Nuclear Magnetic Resonance Spectroscopy and mass spectrometry (NMR/MS) was performed and the interpreted spectra were consistent with cannabis-based flavonoid compositions including Flavone, as identified above, and as shown in step 60. The bioactive cannabis-based flavonoid extracts found bioactive for the prevention and treatment of CNS disorders had the structure of the general formula of FIG. 1.

Given the known structure of the general formula of FIG. 1, a method for synthesizing the same becomes possible. The bioactive cannabis-based flavonoid pharmaceutical composition may be synthesized by the phenylpropanoid metabolic pathway in which the amino acid phenylalanine is used to produce 4-coumaroyl-CoA.

It should now be apparent that the above-described invention provides a pharmaceutical composition for the prevention and treatment of disease with specific cannabis-based flavonoid compounds selected from among the groups of Apigenin, Cannflavin A, Cannflavin B, Cannflavin C, Chrysoeriol, Cosmosiin, Flavocannabiside, Kaempferol, Luteolin, Myricetin, Orientin, Isoorientin (Homoorientin), Quercetin, (+)-Taxifolin, Vitexin, and Isovitexin, a method for prevention and treatment of disease using the specific cannabis-based flavonoid pharmaceutical compositions, a method for isolating the cannabis-based flavonoid pharmaceutical compositions from raw plant material, and a method for synthesizing said specific cannabis-based flavonoid pharmaceutical compositions.

Other embodiments of the invention will be apparent to those skilled in the art from consideration of the specification and practice of the invention disclosed herein. It is intended that the specification, and examples be considered as exemplary only, with a true scope and spirit of the invention being indicated by the claims. In addition, as one of ordinary skill in the art would appreciate, any dimensions shown in the drawings or described in the specification are merely exemplary, and can vary depending on the desired application of the invention. Many variations and modifications of the embodiments described herein will be obvious to one of ordinary skill in the art in light of the above disclosure. The scope of the invention is to be defined only by the claims, and by their equivalents.

STATEMENT OF INDUSTRIAL APPLICABILITY

CNS related conditions including Parkinson's, Alzheimer, Huntington's disease, Multiple sclerosis, Amyotrophic lateral sclerosis (ALS), Hereditary diffuse leukoencephalopathy with spheroids (HDLS) and epilepsy are substantial health problems worldwide. There would be great industrial applicability in the use of a group of cannabis-based flavonoid pharmaceutical compositions including any one or more selected from the group of Apigenin, Cannflavin A, Cannflavin B, Cannflavin C, Chrysoeriol, Cosmosiin, Flavocannabiside, Kaempferol, Luteolin, Myricetin, Orientin, Isoorientin (Homoorientin) Quercetin, (+)-Taxifolin, Vitexin, and Isovitexin, or their synthases, for the prevention and treatment of certain diseases of the CNS system and related disorders.

We claim:

1. A method of treating CNS-related conditions, comprising administering a cannabis-based flavonoid pharmaceutical composition having a specific chemical structure as shown below, or any pharmaceutically acceptable salt thereof:

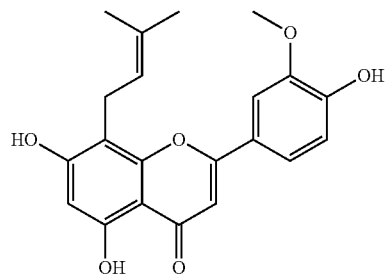 [SMILES: COc1cc(-c2cc(=O)c3c(O)cc(O)c(CC=C(C)C)c3o2)ccc1O]

wherein the CNS-related conditions is selected from the group consisting of Parkinson's disease, Alzheimer's disease, Huntington's disease, Multiple sclerosis, Amyotrophic lateral sclerosis (ALS), Hereditary diffuse leukoencephalopathy with spheroids (HDLS) and epilepsy.

2. The method of claim 1, wherein said compound is administered in a concentration within a range of from 0.1 to 500 mg between 1-6 times per day.

3. The method of claim 1, wherein said compound is administered using a method selected from the group consisting of oral administration, rectal administration, intravenous administration via the epidural muscle, subcutaneous administration, intrauterine administration, via intracerebroventricular injections, and topically.

4. The method of claim 1, wherein said compound is administered in a formulation comprising a carrier, said carrier being selected from the group consisting of: lactose, dextrose, sucrose, sorbitol, mannitol, xylitol, erythritol, maltitol, starches, gum acacia, alginate, gelatin, calcium phosphate, calcium silicate, cellulose, methyl cellulose, microcrystalline cellulose, polyvinylpyrrolidone, water, methyl benzoate, propyl benzoate, talc, magnesium stearate, and mineral oil.

5. The method of claim 1, wherein the CNS-related condition treated by said compound is Alzheimers.

* * * * *